(12) United States Patent
Kang

(10) Patent No.: US 12,121,429 B2
(45) Date of Patent: Oct. 22, 2024

(54) DIAPER SET EQUIPPED WITH EXCRETA INDUCING SEAT

(71) Applicant: Young Ja Kang, Seoul (KR)

(72) Inventor: Young Ja Kang, Seoul (KR)

(*) Notice: Subject to any disclaimer, the term of this patent is extended or adjusted under 35 U.S.C. 154(b) by 420 days.

(21) Appl. No.: 17/689,160

(22) Filed: Mar. 8, 2022

(65) Prior Publication Data

US 2022/0287890 A1    Sep. 15, 2022

(30) Foreign Application Priority Data

Mar. 9, 2021  (KR) .................. 10-2021-0031070

(51) Int. Cl.
*A61F 13/495* (2006.01)
*A61F 13/49* (2006.01)
*A61F 13/56* (2006.01)
*A61F 13/62* (2006.01)

(52) U.S. Cl.
CPC ........ *A61F 13/495* (2013.01); *A61F 13/4906* (2013.01); *A61F 13/5644* (2013.01); *A61F 13/62* (2013.01); *A61F 2013/4953* (2013.01); *A61F 2013/4958* (2013.01)

(58) Field of Classification Search
CPC ........ A61F 2013/15186; A61F 13/4906; A61F 13/49; A61F 13/5644; A61F 13/62; A61F 13/496; A61F 13/82; A61F 2013/4955; A61F 13/49007; A61F 2013/49063; A61F 13/495
See application file for complete search history.

(56) References Cited

U.S. PATENT DOCUMENTS

| | | | | |
|---|---|---|---|---|
| 3,532,093 | A  * | 10/1970 | Rose ..................... | A61F 5/451 604/350 |
| 5,306,266 | A  * | 4/1994 | Freeland ........... | A61F 13/49007 604/385.19 |
| 6,716,204 | B1 * | 4/2004 | D'Acchioli ........... | A61F 13/495 604/385.03 |
| 6,733,482 | B1 * | 5/2004 | Coles ..................... | A61F 13/82 977/841 |
| 9,937,083 | B1 * | 4/2018 | Neuenschwander ... | A61F 13/45 |
| 2004/0153043 | A1 * | 8/2004 | Sugito ................... | A61F 13/495 604/385.27 |
| 2005/0182382 | A1 * | 8/2005 | Bailey ................... | A61F 13/495 604/385.101 |
| 2007/0088305 | A1 * | 4/2007 | Sakano ................. | A61F 13/495 604/385.19 |
| 2007/0088310 | A1 * | 4/2007 | Sugiyama ............. | A61F 13/495 604/385.19 |

(Continued)

*Primary Examiner* — Catharine L Anderson
*Assistant Examiner* — Erin A Kim
(74) *Attorney, Agent, or Firm* — LEX IP MEISTER, PLLC

(57) ABSTRACT

The present invention relates to a diaper set including: a diaper cover; a flap separation type diaper disposed on top of the diaper cover and having a feces bag; and a 'ㄴ'-shaped excreta inducing seat disposed on the rear end of the feces bag of the flap separation type diaper, wherein the diaper cover is separated into a waist belt part and a diaper base part, the flap separation type diaper includes a seat accommodation bag disposed on the rear end of the feces bag, and the 'ㄴ'-shaped excreta inducing seat has an inclined surface slant upward and backward from the rear end of the underside thereof.

17 Claims, 10 Drawing Sheets

(56) References Cited

U.S. PATENT DOCUMENTS

2009/0270825 A1* 10/2009 Wciorka ............... A61F 13/539
                                                      604/378
2014/0257227 A1*  9/2014 Roe .................... A61F 13/4906
                                                      604/385.14

* cited by examiner

DIAPER SET EQUIPPED WITH EXCRETA INDUCING SEAT

TECHNICAL FIELD

The present invention relates to a diaper set having an excreta inducing seat disposed on top of a diaper.

In specific, the present invention relates to a diaper set that is provided with a diaper disposed on top of a diaper cover and having a feces bag and a '⊏'-shaped excreta inducing seat disposed on the rear end of the feces bag of the diaper, wherein the diaper cover includes a waist belt part and a diaper base part detachably attached to each other by means of Velcro tapes, the diaper (a flap separation type diaper or a flap integration type diaper) includes a seat accommodation bag disposed on the rear end of the feces bag, and the '⊏'-shaped excreta inducing seat has an inclined surface slant upward and backward from the rear end of the underside thereof.

BACKGROUND ART

Generally, disposable diapers for babies and adults are used just once and then thrown away, and they serve to absorb excreta such as urine, feces, and the like expelled from a body and contain the absorbed excreta therein to protect a body part like the skin from the excreta. Accordingly, the disposable diapers can prevent the excreta from polluting or wetting a wearer's clothes and surrounding products.

The disposable diaper having such functions typically includes a liquid transmitting top sheet coming into direct contact with a wearer's skin, a bottom sheet for forming an external surface thereof when worn, an absorbent core disposed between the top sheet and the bottom sheet, leg flaps having elastic bodies, and fastening means.

In specific, a typically used disposable diaper includes a diaper body having an absorbent sheet made of a non-woven fabric, a waterproof sheet made of a waterproof material, an absorbent layer made of a super absorbent material, the absorbent sheet and the waterproof sheet being laminated on both sides of the absorbent layer, elastic bodies disposed on the waist, the part between the legs, and the part surrounding the buttocks of the wearer, and adhesive tapes attachedly fixed to one side of the diaper body.

The basic components of the diaper are combined in various ways so that diapers with a variety of shapes may be provided, and among them, a desirable known basic configuration of the disposable diaper is disclosed in U.S. Pat. No. 3,860,003 (dated Jan. 14, 1975).

In this case, the above-mentioned conventional disposable diaper is effective in preventing excreta stacking thereon from leaking to the clothes coming into contact with the edges thereof by means of the leg flaps having elastic bodies that provide barrier films between the edges and the clothes and serve as gaskets around the wearer's legs, but there is a limitation in preventing the excreta in which a lot of water is contained from leaking to the outside only through the leg flaps.

To solve such a problem, barrier bodies with elastic bodies are additionally disposed inside the leg flaps, and accordingly, various barrier bodies are suggested in conventional technologies.

For example, a flap having an elastic member, which is disposed inside a leg flap, is disclosed in Korean Patent Application Laid-open No. 1993-0000085, a barrier cuff disposed between a leg flap and an absorbent core is disclosed in Korean Patent Application Laid-open No. 1994-0008959, and a double poop band having the same height is disclosed in Korean Patent Application Laid-open No. 1995-0008172.

Among the components of the disposable diapers, the top sheet is soft, gives no irritation to a wearer's skin, and has physical properties of passing liquid excreta therethrough to introduce the excreta into the absorbent core. Further, the top sheet is made of various materials, such as a porous plastic film, a natural fiber, a synthetic fiber, and a mixture of the natural fiber and the synthetic fiber.

Further, the absorbent core serves to absorb and contain the liquid excreta, and an absorbent material of the absorbent core includes a fluff pulp, a super absorbent polymer, and a tissue for packing the fluff pulp and the supper absorbent polymer. The absorbent core rapidly absorbs the excreta passing through the liquid transmitting top sheet and contains the excreta to prevent the excreta from coming into contact with the wearer's skin, and the sizes, shapes, structures, and absorbing capabilities of the absorbent core may be determined appropriately according to baby and adult wearers.

The bottom sheet does not transmit liquid therethrough to prevent the excreta absorbed to the absorbent core from polluting or wetting the wearer's cloths coming into contact with the diaper and the produce like a bed sheet. Accordingly, the bottom sheet desirably does not transmit liquid and transmits gas, and typically, a plastic film is used as the bottom sheet. Recently, a material made by attaching a non-woven fabric to a polyethylene film is widely used as the bottom sheet.

The leg flaps are located close to the vertical edges of the diaper so that when the diaper is worn, it can be fixed to the wearer's legs, and each leg flap has a side flap and a flap elastics, which is disclosed in detail in U.S. Pat. No. 3,860,003.

The poop band is disposed close to the absorbent core of the typical disposable diaper to prevent the excreta (feces and urine) not absorbed to the absorbent core from leaking to the outside and is made of a liquid transmitting material or a liquid non-transmitting material.

When the conventional disposable diapers are worn, however, skin problems, such as skin prurithus (itch), skin erytherma, and skin excoriation may be often caused, which give severe pains and unpleasant feelings to wearers.

Such the skin problems may be caused by skin irritation due to ammonia generated from urine and feces, by skin irritation due to activation of germs on skin surface in a state where the urine and feces come into direct contact with the skin or the urine and feces absorbed to the absorbent core come into contact with the skin, by physical and chemical frictions between the disposable diaper and the wearer's skin, and by an excessive amount of water generated while being worn.

To solve such problems, there are suggested Korean Patent No. 10-1141853 (entitled 'Disposable diaper with excreta storage chamber'), Korean Utility Model Registration No. 20-0467843 (entitled 'Excreta bag exchange type diaper'), Korean Patent Application Laid-open No. 10-2015-0042920 (entitled 'Excreta bag detachment type diaper'), and Korean Patent Application Laid-open No. 10-2000-0068444 (entitled 'Absorbent product having leakage prevention dam'), which are filed by the same applicant as the present invention, and there is suggested Japanese Patent Application Laid-open No. 2005-144130 (entitled 'Excreta auxiliary tool').

According to the conventional technology as disclosed in Korean Patent No. 10-1141853 (entitled 'Disposable diaper with excreta storage chamber'), an excreta storage bag is disposed on a center portion formed by bonding a bottom sheet and a top sheet, a cover plate is fixed at the center portion on the top sheet and has an introduction hole with a temporary blocking paper attached thereto, and an excreta storage chamber is formed between the top sheet and the cover plate and has an absorbent member.

According to the conventional technology as disclosed in Korean Patent No. 10-1141853 (entitled 'Disposable diaper with excreta storage chamber'), in specific, the bottom sheet and the top sheet formed integrally with each other each include a rear portion, a center portion, and a front portion, leakage prevention side flaps are disposed on both sides of the top sheet, and bands are disposed on both sides of the rear portion and have adhesive members disposed thereon. In this case, each band has an elastic member disposed on the bottom end thereof, and front cover plates are disposed on both sides of the intermediate portion of the center portion and the front portion and have adhesive members disposed thereon. Further, the excreta storage chamber is formed on the center portion between the bottom sheet and the top sheet through the excreta introduction hole of the center portion of the top sheet.

According to Korean Utility Model Registration No. 20-0467843 (entitled 'Excreta bag exchange type diaper') and Korean Patent Application Laid-open No. 10-2015-0042920 (entitled 'Excreta bag detachment type diaper'), an excreta bag installation hole is formed on the center portion of a diaper, and accordingly, an excreta bag is detachably mounted on the excreta bag installation hole.

Even though the conventional diapers have the excreta storage chambers or bags, however, urine and feces come into direct contact with the wearer's skin or they come into contact with the skin in a state of being absorbed to the absorbent core, thereby causing skin problems due to activities of germs on the wearer's skin.

According to Korean Patent Application Laid-open No. 10-2000-0068444 (entitled 'Absorbent product having leakage prevention dam'), a cylindrical leakage prevention dam is installed on a range from top surface of an absorbent product (diaper) to the rear portion thereof (corresponding to a wearer's buttock rear portion), but when the absorbent product is worn, the leakage prevention dam cannot be fixed well. If the wearer moves, accordingly, the worn position of the absorbent product may easily change and move, thereby failing to efficiently treat the wearer's urine and feces.

According to Japanese Patent Application Laid-open No. 2005-144130 (entitled 'Excreta auxiliary tool'), a diaper has an oval-shaped air bag as a space portion formed on the center thereof, and if it is desired to use the diaper, air has to be filled in the oval-shaped air bag inconveniently. After the use of the diaper, besides, the air has to be inconveniently removed from the air bag stained with urine and feces. When the diaper is worn, also, the excreta auxiliary tool cannot be fixed well, and if the wearer moves, the worn position of the absorbent product may easily change and move, thereby failing to efficiently treat the wearer's urine and feces.

A diaper protected by a diaper cover is disclosed in Korean Utility Model Registration No. 20-0411904 (entitled 'Diaper'), and according to the conventional diaper, a pad is detachably mounted on top of a diaper cover by means of attaching means such as Velcro tapes. In this case, the pad is just exchanged with new one on the diaper cover and then used (worn).

DISCLOSURE

Technical Subject

Accordingly, the present invention has been made to solve the above-mentioned problems, and it is an object of the present invention to provide a diaper set with an excreta inducing seat.

It is another object of the present invention to provide a diaper set that is capable of having a diaper with a feces bag disposed on top of a diaper cover and a 'ᄃ'-shaped excreta inducing seat disposed on the rear end of the feces bag of the diaper, wherein the diaper cover is separated into a waist belt part and a diaper base part detachably attached to each other by means of Velcro tapes, the diaper (flap separation type diaper or flap integration type diaper) includes a seat accommodation bag disposed on the rear end of the feces bag to accommodate the 'ᄃ'-shaped excreta inducing seat therein, and the 'ᄃ'-shaped excreta inducing seat has an inclined surface slant upward and backward from the rear end of the underside thereof.

It is yet another object of the present invention to provide a diaper set that is capable of having a diaper cover separated into a waist belt part and a diaper base part detachable to each other by means of Velcro tapes, so that in a state where the waist belt part and the diaper base part are coupled to each other, they are all used when a diaper is worn, and in a state where the waist belt part and the diaper base part are separated from each other, the waist belt part is used as a waist belt for protecting a wearer's waist, a diaper (a flap separation type diaper or flap integration type diaper) with a seat accommodation bag disposed on the rear end of a feces bag, so that if it is desired to wear the diaper, a 'ᄃ'-shaped excreta inducing seat is accommodated in the seat accommodation bag to provide a comfortable sense of wearing for the wearer, and the 'ᄃ'-shaped excreta inducing seat having an inclined surface slant upward and backward from the rear end of the underside thereof, so that in a state where the diaper is worn after the excreta inducing seat has been inserted into the seat accommodation bag, even though the wearer lies down for long hours, the excreta inducing seat is brought into close contact with the wearer's buttocks and has no reluctance to the diaper and the wearer, thereby improving a sense of wearing, and even though the wearer expels feces, the feces passes through the excreta inducing seat and is accommodated in the feces bag, thereby allowing the wearer to be still at a cleaned state.

Technical Solution

To accomplish the above-mentioned objects, according to the present invention, there is provided a diaper set including: a diaper cover; a flap separation type diaper disposed on top of the diaper cover and having a feces bag; and a 'ᄃ'-shaped excreta inducing seat disposed on the rear end of the feces bag of the flap separation type diaper, wherein the diaper cover is separated into a waist belt part and a diaper base part, the flap separation type diaper includes a seat accommodation bag disposed on the rear end of the feces bag, and the 'ᄃ'-shaped excreta inducing seat has an inclined surface slant upward and backward from the rear end of the underside thereof.

Advantageous Effects

According to the present invention, the diaper set is configured to have the diaper with the feces bag disposed on top of the diaper cover and the 'ᄃ'-shaped excreta inducing seat disposed on the rear end of the feces bag of the diaper, wherein the diaper cover is separated into the waist belt part and the diaper base part detachably attached to each other by means of the Velcro tapes, the diaper (flap separation type diaper or flap integration type diaper) includes the seat accommodation bag disposed on the rear end of the feces bag to accommodate the 'ᄃ'-shaped excreta inducing seat therein, and the 'ᄃ'-shaped excreta inducing seat has the inclined surface slant upward and backward from the rear end of the underside thereof.

In specific, the diaper set according to the present invention is characterized in that the diaper cover is separated into the waist belt part and the diaper base part detachable to each other by means of the Velcro tapes, so that in a state where the waist belt part and the diaper base part are coupled to each other, they are all used when a diaper is worn, and in a state where the waist belt part and the diaper base part are separated from each other, the waist belt part is used as a waist belt for protecting a wearer's waist; the diaper (the flap separation type diaper or the flap integration type diaper) has the seat accommodation bag disposed on the rear end of the feces bag, so that if it is desired to wear the diaper, the 'ᄃ'-shaped excreta inducing seat is accommodated in the seat accommodation bag to provide a comfortable sense of wearing for the wearer and to prevent escape from the seat accommodation bag even after the wearing, thereby allowing the wearer to easily and pleasantly expel feces; and the 'ᄃ'-shaped excreta inducing seat has the inclined surface slant upward and backward from the rear end of the underside thereof, so that in a state where the diaper is worn after the excreta inducing seat has been inserted into the seat accommodation bag, even though the wearer lies down for long hours, the excreta inducing seat is brought into close contact with the wearer's buttocks and has no reluctance to the diaper and the wearer, thereby improving a sense of wearing, and even though the wearer expels feces, the feces passes through the excreta inducing seat and is accommodated in the feces bag, thereby allowing the wearer to be still at a cleaned state.

BEST MODE FOR INVENTION

Objects, characteristics and advantages of the present invention will be more clearly understood from the detailed description as will be explained below and the attached drawings.

FIGS. 1 to 8 are exemplary views showing a diaper set equipped with an excreta inducing seat according to embodiments of the present invention.

Figure 1:
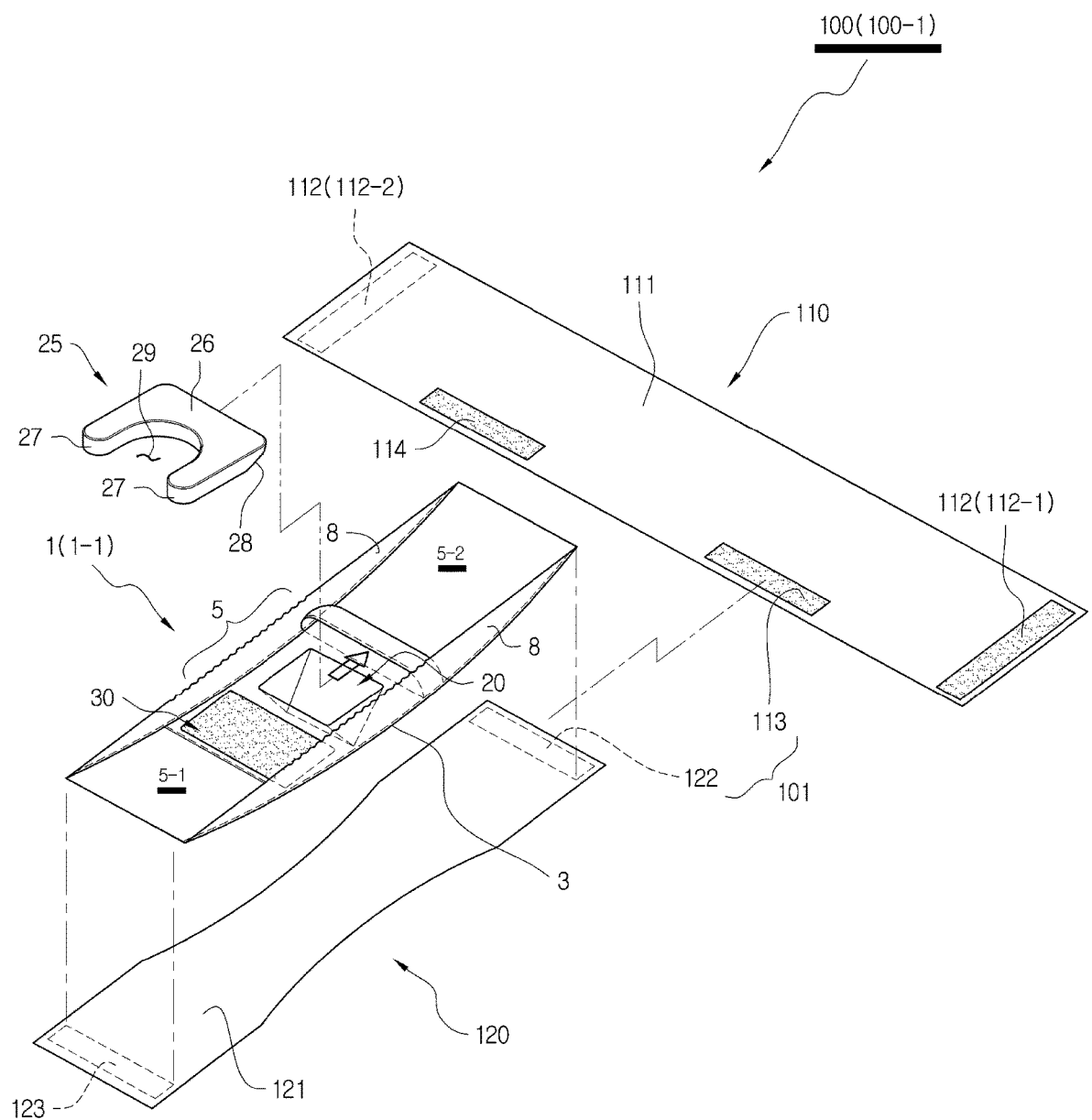
FIG. 1 is an exploded perspective view showing a diaper set equipped with an excreta inducing seat according to an embodiment of the present invention.
Figure 2A:
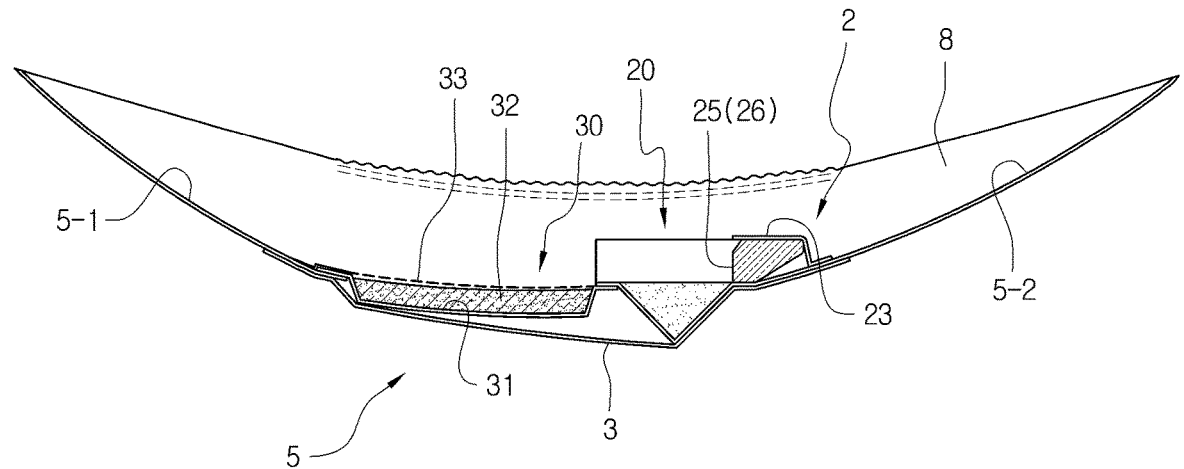
FIGS. 2a and 2b are side and enlarged sectional views showing the diaper set equipped with an excreta inducing seat as shown in FIG. 1.
Figure 2B:
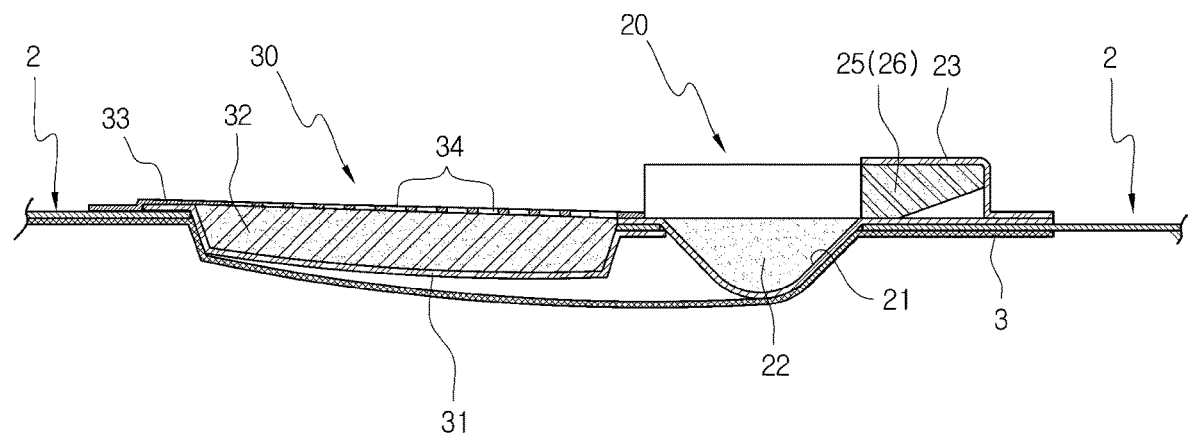
Figure 3:
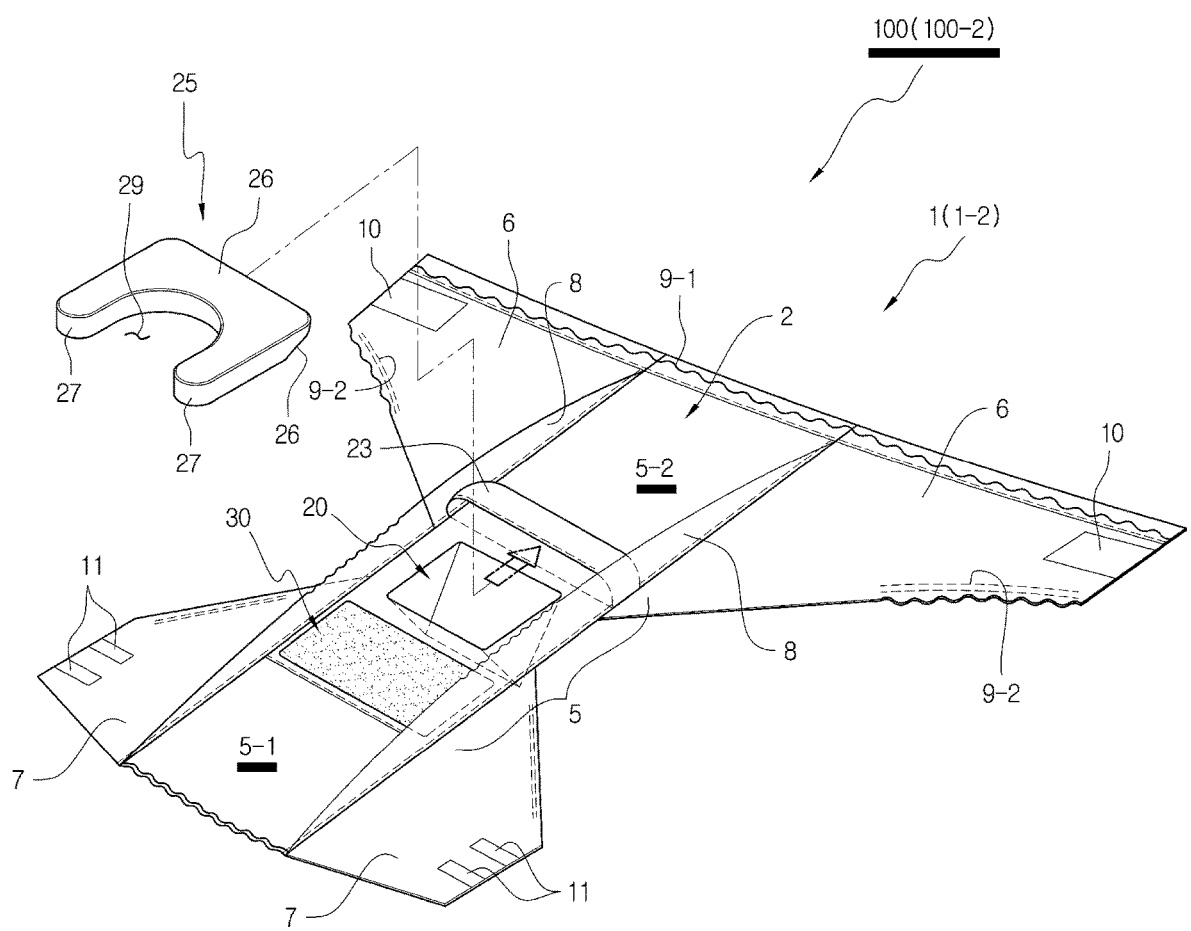
FIG. 3 is a perspective view showing a diaper set equipped with an excreta inducing seat according to another embodiment of the present invention.
Figure 4:
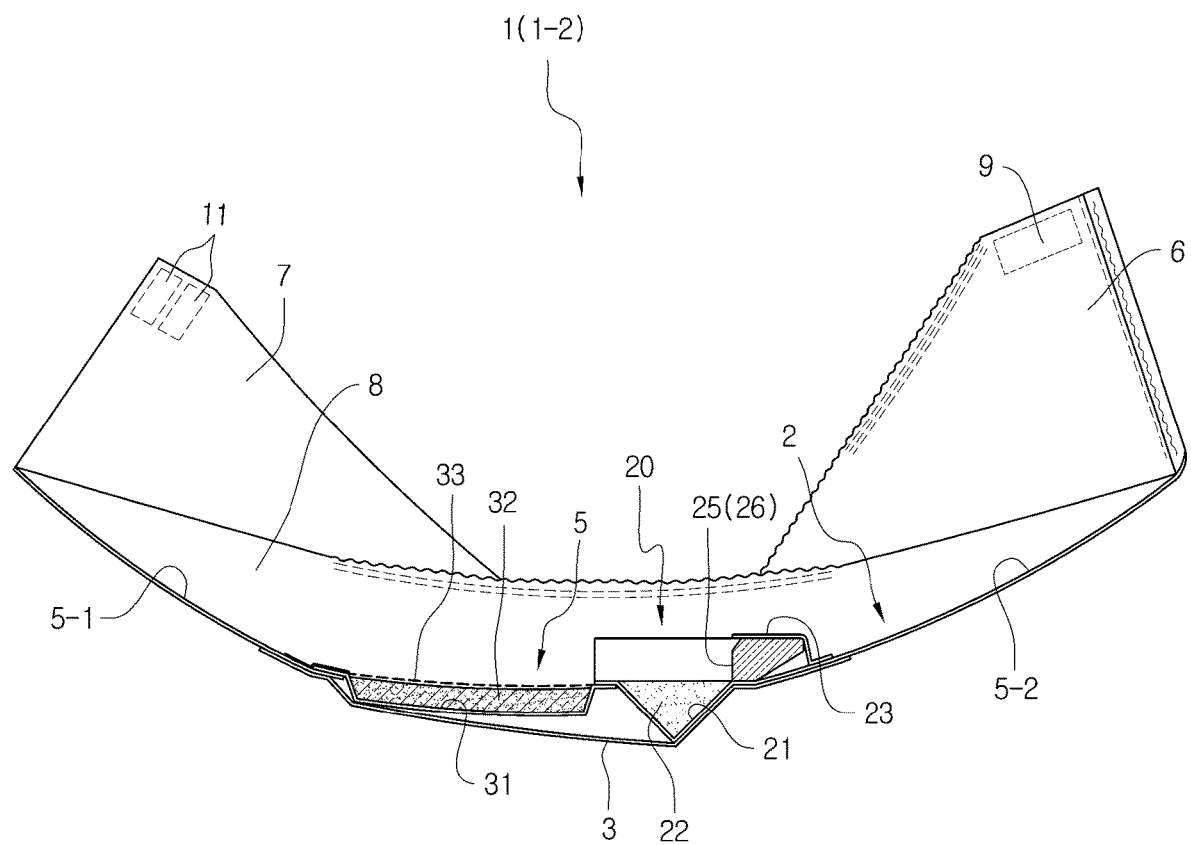
FIG. 4 is a side sectional view showing the diaper set equipped with an excreta inducing seat as shown in FIG. 3.

FIG. 1 is an exploded perspective view showing a diaper set equipped with an excreta inducing seat according to an embodiment of the present invention and FIGS. 2a and 2b are side and enlarged sectional views showing the use states of the waist belt part separated from the diaper set according to the present invention. FIGS. 3 and 4 are perspective and side sectional views showing a diaper set equipped with an excreta inducing seat according to another embodiment of the present invention.

Figure 5A:
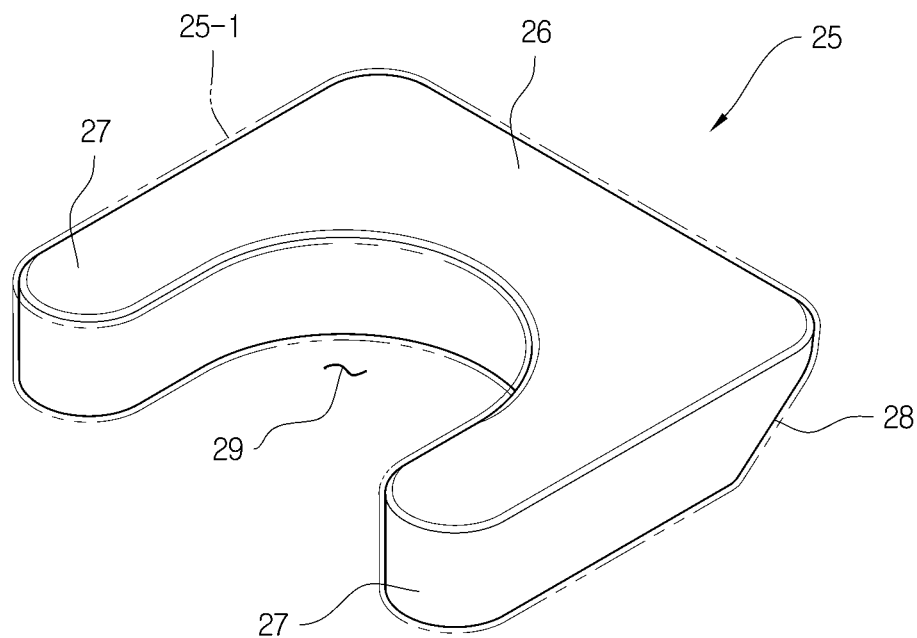
FIGS. 5a to 5d are front, bottom, and side sectional views showing the excreta inducing seat of each diaper set according to the embodiments of the present invention.
Figure 5B:
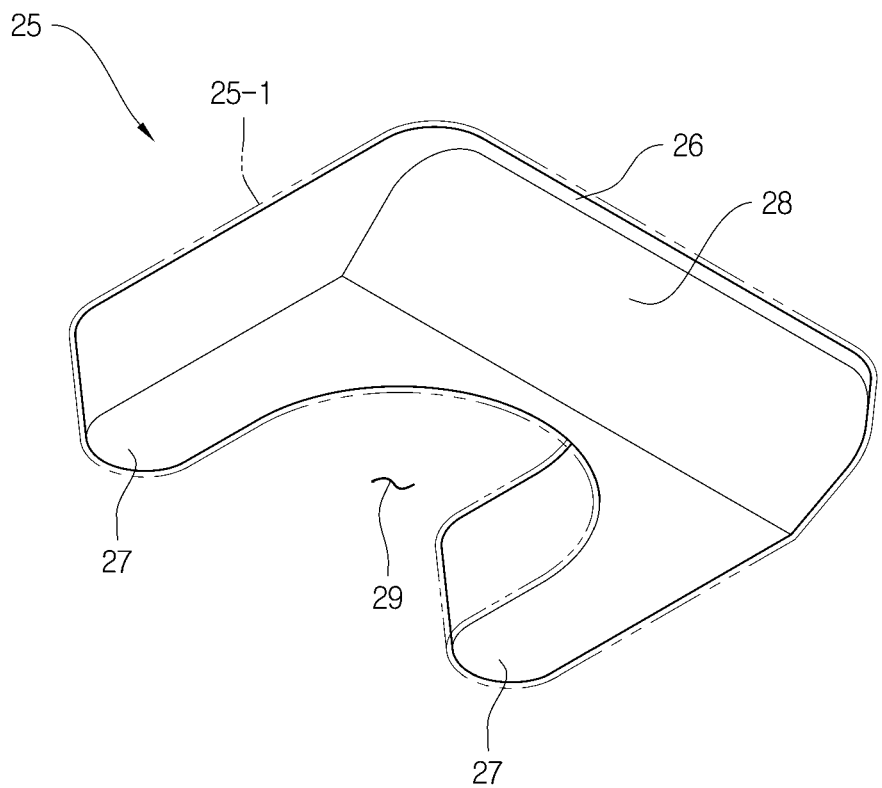
Figure 5C:
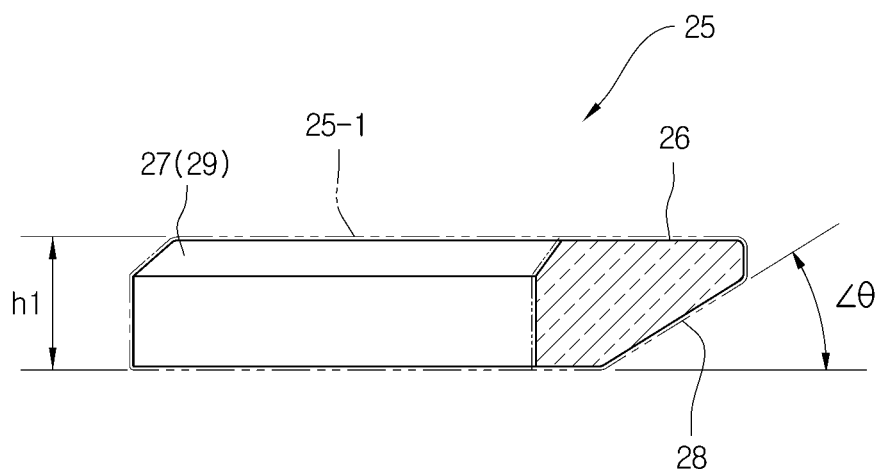
Figure 5D:
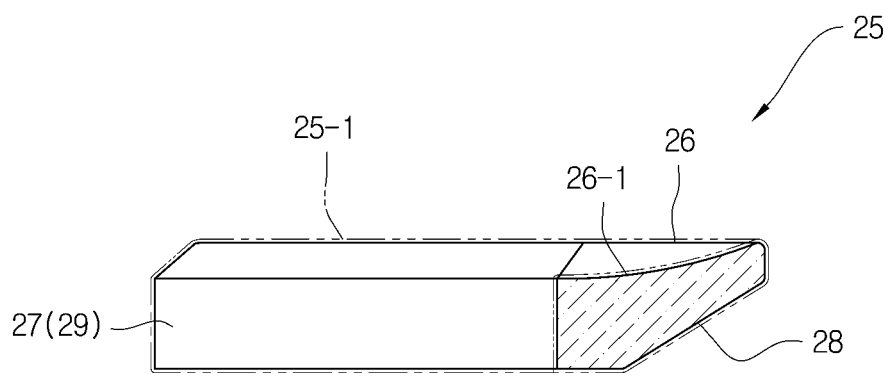
Figure 6A:
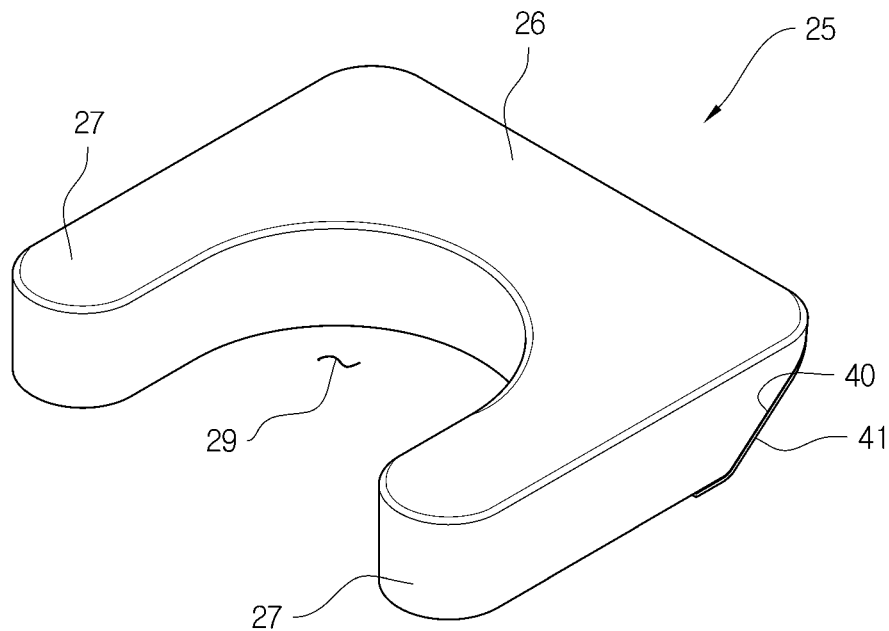
FIGS. 6a to 6d are top and bottom perspective views and side sectional views showing examples of the excreta inducing seat according to the embodiments of the present invention.
Figure 6B:
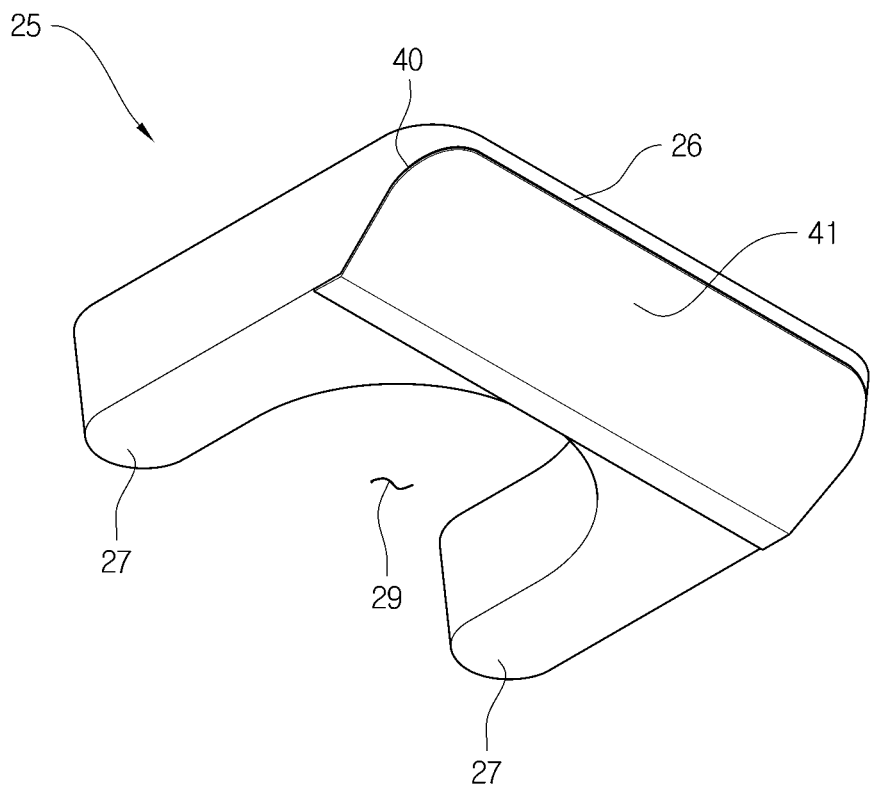
Figure 6C:
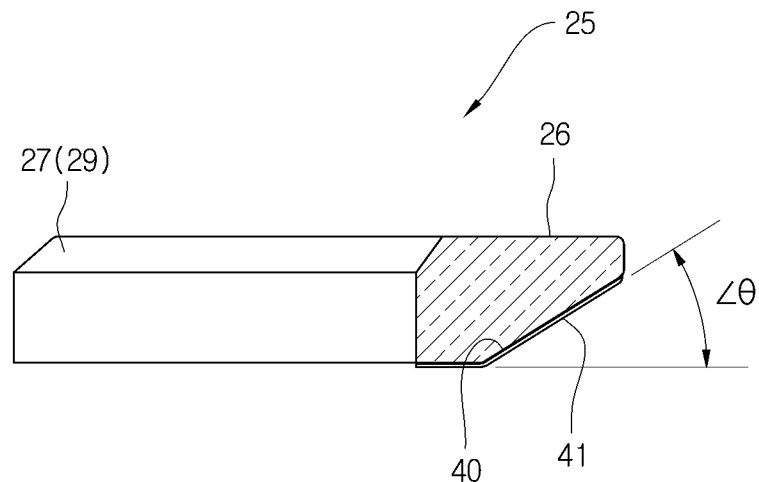
Figure 6D:
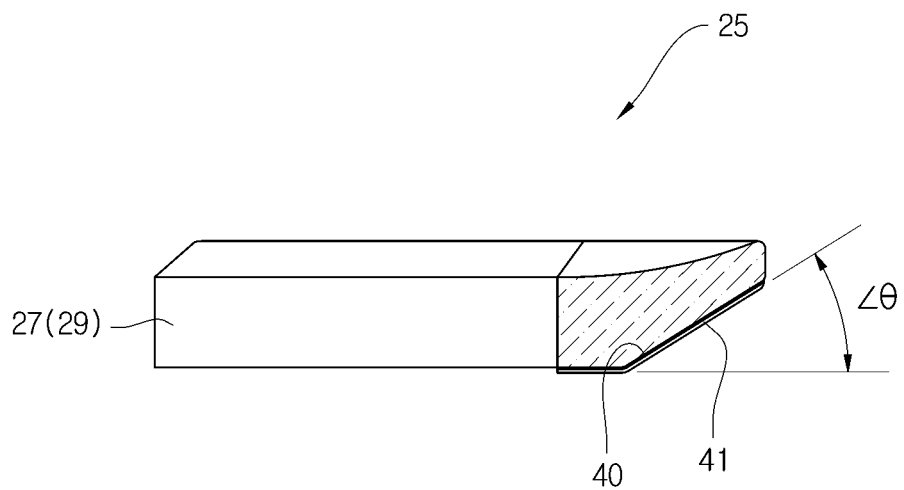
Figure 7A:
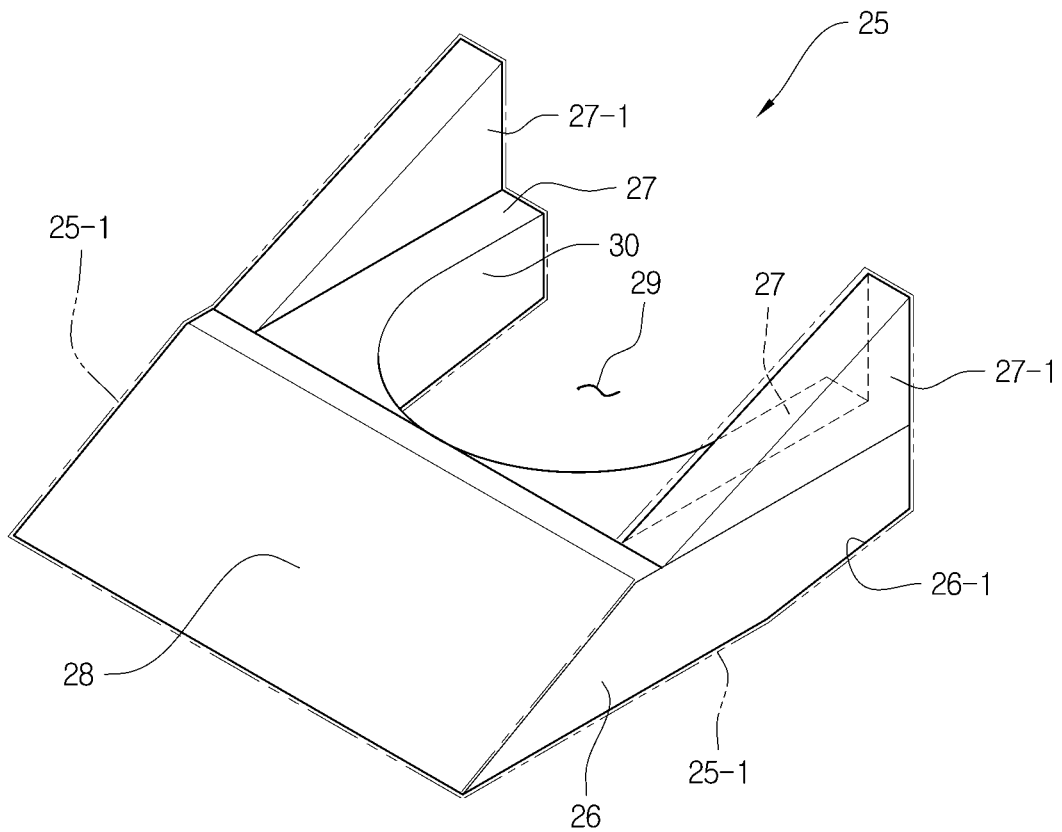
FIGS. 7a to 7c are reversed perspective and side sectional views other examples of the excreta inducing seat according to the embodiments of the present invention.
Figure 7B:
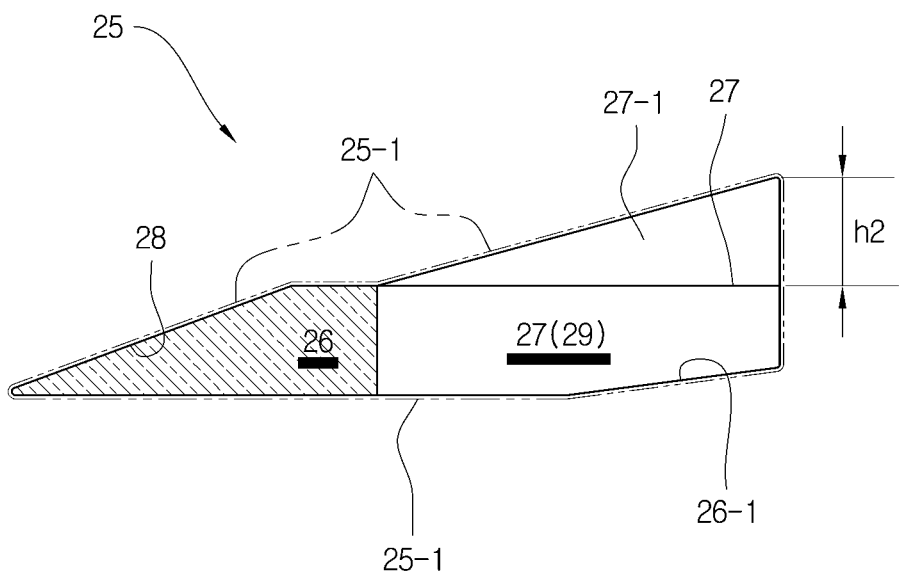
Figure 7C:
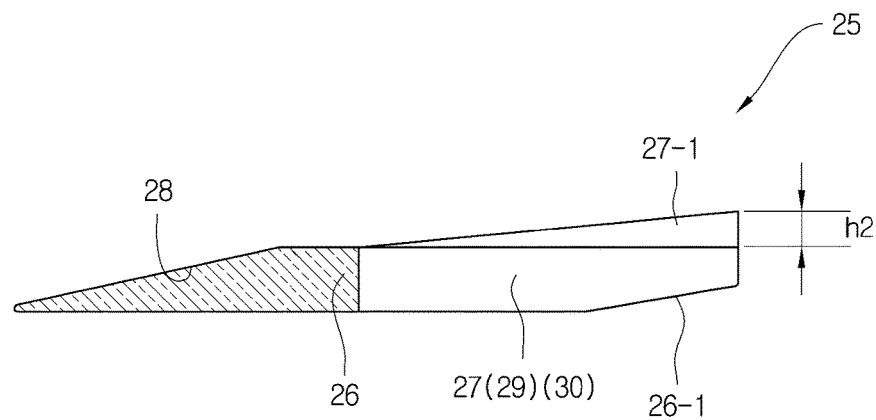

FIGS. 5a to 5d are exemplary views (front, bottom, and side sectional views) showing the excreta inducing seat removed from each diaper set according to the embodiments of the present invention, FIGS. 6a to 6d are exemplary views (top and bottom perspective and side sectional views) showing examples of the excreta inducing seat according to the embodiments of the present invention, and FIGS. 7a to 7c are reversed perspective and side sectional views other examples of the excreta inducing seat according to the embodiments of the present invention.

Figure 8:
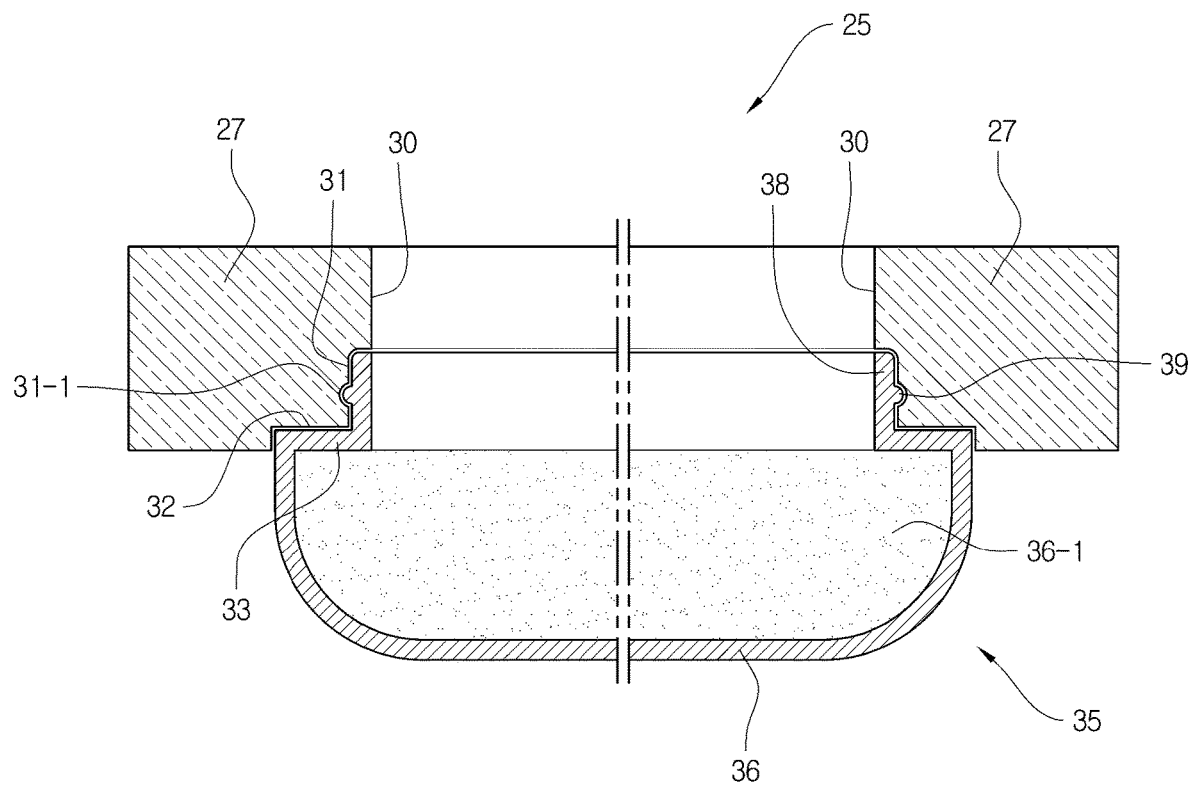
FIG. 8 is a sectional view showing a state where a detachable feces accommodator is mounted directly on an open portion inner peripheral surface of the excreta inducing seat in the diaper set according to the present invention.

FIG. 8 is a sectional view showing a state where a detachable feces accommodator is mounted directly on an open portion inner peripheral surface f the excreta inducing seat in the diaper set according to the present invention.

First, an explanation of a configuration of a diaper set equipped with an excreta inducing seat according to an embodiment of the present invention will be given.

As shown in FIGS. 1 to 2b, a diaper set 100-1 according to an embodiment of the present invention largely includes a waist belt part 110, a diaper base part 120, a diaper 1-1 seated on top of the diaper base part 120, and an excreta inducing seat 25 coupled to the diaper 1-1.

A diaper cover 101 is separated into the waist belt part 110 and the diaper base part 120.

The waist belt part 110 includes a waist belt 111 with a rectangular shape whose length is long and width is relatively smaller than the length, waist belt fastening Velcro tapes 112-1 and 112-2 attached to surfaces corresponding to each other on both ends of the waist belt 111 to allow the waist belt 111 to be worn gently on a wearer's waist.

Further, the waist belt part 110 includes a pair of diaper base fastening Velcro tapes 113 and 114 spaced apart from each other on left and right sides thereof and attached to the underside of one surface of the waist belt 111 to allow a diaper base 121 as will be discussed later on which the flap separation type diaper 1-1 is disposed to be easily worn between the part between the wearer's legs in a state where the waist belt 111 is worn on the wearer's waist.

In specific, the waist belt 111 may be worn on the waist even while the diaper set is being not worn and thus used as a belt for protecting the wearer's waist.

The diaper base part 120 detached from the waist belt part 110 includes the diaper base 121 whose length and width relatively larger than those of the flap separation type diaper 1-1 to sufficiently cover the flap separation type diaper 1-1 therewith and fastening Velcro tapes 122 and 123 attached to top and bottom ends of the diaper base 121 to be detachably attached to the diaper base fastening Velcro tapes 113 and 114 of the waist belt 111.

The flap separation type diaper 1-1 seated on top of the diaper base 121 of the diaper base part 120 is configured as follows.

The flap separation type diaper 1-1 includes a top sheet constituting a diaper body, leakage prevention flaps 8 disposed on both side end portions of the top sheet 2 in parallel with each other, a front surface 5-1 and a rear surface 5-2 formed on the front and rear sides of a center portion 5 of the top sheet 2, and a feces accommodator 20 disposed on the rear side of the center portion 5 and having a feces bag 21 filled with an absorbent member 22.

Further, the flap separation type diaper 1-1 includes a urine accommodator 30 disposed on the front side of the feces accommodator 20 and having a urine bag 31 filled with an absorbent member 32 and a urine accommodator cover sheet 33 attached to the surface thereof and having fine pores 34 formed thereon.

Further, the flap separation type diaper 1-1 includes a bottom sheet 3 with an adhesive (not shown) applied to a longitudinal center line thereof and a release paper attached to the adhesive, and in a state where the release paper is removed, the flap separation type diaper 1-1 is easily attached to the diaper base 121 by means of the adhesive. Also, the attached state can be prevented from being released or the flap separation type diaper 1-1 can be prevented from being separated from the diaper base 121.

FIGS. 3 and 4 are perspective and side sectional views showing a diaper set 100-2 equipped with an excreta inducing seat according to another embodiment of the present invention, and the diaper set 100-2 largely includes a flap integration type diaper 1-2 and an excreta inducing seat 25 coupled to the flap integration type diaper 1-2.

The flap integration type diaper 1-2 is configured as follows.

The flap integration type diaper 1-2 includes a top sheet 2 constituting a diaper body, leakage prevention flaps 8 disposed on both side end portions of the top sheet 2 in parallel with each other, and a front surface 5-1 and a rear surface 5-2 formed on the front and rear sides of a center portion 5 of the top sheet 2.

Further, the flap integration type diaper 1-2 includes band flaps 7 and 6 formed integrally with both sides of the front surface 5-1 and both sides of the rear surface 5-2 of the top sheet 2 and having adhesive members 11 and 10 disposed thereon and elastic members 9-1 and 9-2 disposed on appropriate positions of the band flaps 6 of the rear surface 5-2.

The above-mentioned configurations of the flap separation type diaper 1-1 and the flap integration type diaper 1-2 are typically known, and accordingly, a detailed explanation on their configuration will be avoided.

As shown in FIGS. 3 and 4, the flap integration type diaper 1-2 of the diaper set 100-2 according to another embodiment of the present invention includes a feces accommodator 20 disposed on the rear side of the center portion 5 and having a feces bag 21 filled with an absorbent member 22 and a urine accommodator 30 disposed on the front side of the feces accommodator 20 and having a urine bag 31 filled with an absorbent member 32 and a urine accommodator cover sheet 33 attached to the surface thereof and having fine pores 34 formed thereon.

In specific, the flap integration type diaper 1-2 further includes a seat accommodation bag 23 attached to the rear side of top of the feces bag 21 of the feces accommodator 20 and open toward the feces bag 21 to allow the excreta inducing seat 25 to be easily accommodated in the seat accommodation bag 23, and the seat accommodation bag 23 is made of the same material (non-woven fabric and the like) as the top sheet 2 or an elastic material to cause no trouble on the wearer's skin.

Further, the flap integration type diaper 1-2 includes a bottom sheet 3 disposed on the underside of the center portion 5 to prevent the feces bag 21 of the feces accommodator 20 and the urine bag 31 of the urine accommodator 30 from being exposed to the outside and to supportedly protect the feces bag 21 and the urine bag 3.

The excreta inducing seat 25 coupled to the seat accommodation bag 23 formed on the flap integration type diaper 1-2 of the diaper set 100-2 according to another embodiment of the present invention is configured as shown in FIGS. 5a to 5d and FIGS. 6a to 6d.

As shown in FIGS. 5a to 5d and FIGS. 6a to 6d, the excreta inducing seat 25 is generally ∩-shaped, while having a buttock rear surface stand 26 and buttock side surface stands 27 extending from both sides of the buttock rear surface stand 26 in parallel with each other, and further, the excreta inducing seat 25 includes an open portion 29 formed on the center thereof and an inclined surface 28 slant upward and backward from the rear end of the underside of the buttock rear surface stand 26.

As the excreta inducing seat 25 is ∩-shaped through the buttock rear surface stand 26 and the buttock side surface stands 27 extending from on both sides of the buttock rear surface stand 26 in parallel with each other, accordingly, the excreta inducing seat 25 completely supports the wearer's buttocks and the buttock sides thereagainst, and further, as the excreta inducing seat 25 has the open portion 29 formed on the center thereof, there is no reluctance on the part (groin) between the wearer's legs.

The excreta inducing seat 25 is made of a foamed resin, silicone, a synthetic resin, rubber, and the like, thereby providing a soft sense of wearing and a given buffering force capable of absorbing the wearer's weight and external impacts.

As shown in FIGS. 5d and 6d, the excreta inducing seat further includes a curvedly concave groove 26-1 formed gently on top surface of the buttock rear surface stand 26, thereby providing good contact with the skin.

The inclined surface 28 slant from the rear end of the underside of the buttock rear surface stand 26 has a given angle $\angle \theta$ between 10 and 45°, desirably between 20 and 35°, so that in a state where the wearer lies down or sits, he or she does not feel any sense of difference or reluctance, while is wearing the excreta inducing seat 25.

In addition, the excreta inducing seat 25 has a height h1 in the range between 5 and 40 mm, desirably, various heights of 10 mm, 15 mm, 20 mm, 25 mm, and 30 mm, so that the height of the excreta inducing seat 25 is freely determined in accordance with baby and adult wearers.

Further, as shown in FIGS. 5a to 5d, the excreta inducing seat 25 according to the present invention further includes a coated film 25-1 applied to the whole external surfaces thereof. Even though not shown, otherwise, a coated film 25-1 may be applied to tops of the buttock rear surface stand 26 and the buttock side surface stands 27 or tops of only the buttock side surface stands 27.

Like this, if the coated film 15-1 is applied to the whole external surfaces of the excreta inducing seat 25, to tops of the buttock rear surface stand 26 and the buttock side surface stands 27, or to tops of only the buttock side surface stands 27 to the form of a non-woven fabric, a fabric, a paper sheet, and the like, skin troubles caused by the contact with the skin can be prevented while the excreta inducing seat 25 is being worn.

Further, as shown in FIGS. 6a to 6d, the excreta inducing seat 25 according to the present invention further includes an adhesive layer 40 applied to the underside of the buttock rear surface stand 26 and the inclined surface 28 and a release paper 41 attached to the adhesive layer 40.

Even though in specific not shown, the adhesive layer 40 may be applied to the undersides of the buttock side surface stands 27, the underside of the buttock rear surface stand 26, and the inclined surface 28, and next, the release paper 41 is attached to the adhesive layer 40. Otherwise, the adhesive layer 40 may be applied to the undersides of the buttock side surface stands 27 and the underside of the buttock rear surface stand 26, and next, the release paper 41 is attached to the adhesive layer 40.

Like this, if the adhesive layer 40 is applied to the underside of the buttock rear surface stand 26 and the inclined surface 28, to the undersides of the buttock side surface stands 27, the underside of the buttock rear surface stand 26, and the inclined surface 28, or to the undersides of the buttock side surface stands 27 and the underside of the buttock rear surface stand 26 and the release paper 41 is further attached to the adhesive layer 40, the excreta inducing seat 25 is firmly attached to the outside surface of top side of the feces accommodator 20 by means of the adhesive layer 40 when the excreta inducing seat 25 is disposed on top side of the feces accommodator 20 in a state of removing the release paper 41 from the adhesive layer 40, so that when the wearer moves (tosses and turns), the excreta inducing seat 25 can be prevented basically from escaping from the feces accommodator 20 or from being deformed therein.

FIGS. 7a to 7c are reversed perspective and side sectional views other examples of the excreta inducing seat 25 according to the embodiments of the present invention.

As shown, an excreta inducing seat 25 includes an inclined surface 28, buttock side surface stands 27 extending from both sides of the inclined surface 28, triangular buttock stand protrusion pieces 27-1 protruding from the outer edges of the buttock side surface stands 27 in the same direction (on the undersides of the buttock side surface stands 27) as the inclined surface 28, and curvedly inclined surfaces 26-1 formed on the opposite surfaces (top surfaces) of the buttock side surface stands 27 to the triangular buttock stand protrusion pieces 27-1, and the triangular buttock stand protrusion pieces 27-1 protruding from the outer edges of the buttock side surface stands 27 are desirably kept to a height h2 between 5 and 30 mm in consideration of babies and adults.

If the excreta inducing seat 25 as shown in FIGS. 7a to 7c is provided, it turns over and is thus disposed in the seat accommodation bag 23 of the flap separation type diaper 1-1 or the flap integration type diaper 1-2.

Like this, if the excreta inducing seat 25 as shown in FIGS. 7a to 7c turns over and is thus disposed in the seat accommodation bag 23, the buttocks of the wearer are supported against the inclined surface 28 and the triangular buttock stand protrusion pieces 27-1, and accordingly, the wearer's anus is located on the open portion 29 to allow the wearer to easily expel feces, so that the feces is accommodated gently in the feces accommodator 20 through the open portion 29, and even though the wearer expels the feces, a clean and fresh state can be maintained in the diaper set.

FIG. 8 is a sectional view showing a state where a detachable feces accommodator 35 is mounted directly on an open portion inner peripheral surface 30 of the excreta inducing seat 25 in the diaper set according to the present invention.

The excreta inducing seat 25 is configured to allow the underside of the open portion inner peripheral surface 30 to be connected to a vertically concave fastening surface 31 and a horizontally concave fastening surface 32, and in this case, the vertically concave fastening surface 31 has a concave fastening groove 31-1 formed thereon.

The feces accommodator 35, which is coupled to the vertically concave fastening surface 31 on which the concave fastening groove 31-1 is formed and to the horizontally concave fastening surface 32, includes a cylindrical or square-shaped circular fastening protrusion rim 38 with a fastening protrusion piece 39 formed on the outer peripheral surface thereof, a flange 33 formed unitarily with the bottom end of the outer surface of the circular fastening protrusion rim 38, and a feces container 36 disposed unitarily with the underside of the flange 33 and having an absorbent member 36-1 filled therein.

If the feces accommodator 35 is detachably disposed in the open portion inner peripheral surface 30 of the excreta inducing seat 25, the excreta inducing seat 25 to which the feces container 36 is coupled may be installed on a typical diaper (not shown) with no feces accommodator 20.

Hereinafter, the use states of the flap separation type diaper 1-1 and the flap integration type diaper 1-2 of the diaper sets 100-1 and 100-2 according to the present invention will be explained.

First, the use state of the flap separation type diaper 1-1 of the diaper set 100-1 according to the present invention as shown in FIGS. 1 to 2b will be explained.

The release paper (not shown) attached to the adhesive (not shown) applied to the longitudinal center line of the bottom sheet 3 of the flap separation type diaper 1-1 is removed, and next, the adhesive is bonded to the diaper base 121 so that the flap separation type diaper 1-1 is attached to the diaper base 121.

In a state where the flap separation type diaper 1-1 is attached to the diaper base 121, the excreta inducing seat 25 is coupled to the seat accommodation bag 23 of the flap separation type diaper 1-1, and in this case, the buttock rear surface stand 26 and the inclined surface 28 are insertedly coupled to the seat accommodation bag 23.

When the excreta inducing seat 25 is coupled to the seat accommodation bag 23, the release paper 41 attached to the inclined surface 28 of the excreta inducing seat 25 is removed, and otherwise, if the release paper (not shown) is attached to the adhesive layer applied to the undersides of the buttock rear surface stand 26 and the buttock side surface stands 27, the release paper is removed. Next, the buttock rear surface stand 26 and the inclined surface 28 are insertedly coupled to the seat accommodation bag 23.

After that, the waist belt 111 of the waist belt part 110 is put around the wearer's waist and worn on the waist by fastening the waist belt fastening Velcro tapes 112-1 and 112-2 disposed on both ends of the waist belt 111 to each other, and in this case, the waist belt fastening Velcro tapes 112-1 and 112-2 are located on one side of the wearer.

In a state where the waist belt 111 is put around the wearer's waist, the fastening Velcro tape 122 of the fastening Velcro tapes 122 and 123, which is disposed on the side of the diaper base 121 to which the flap separation type diaper 1-1 is attached, is attached to the diaper base fastening Velcro tape 113 of the diaper base fastening Velcro tapes 113 and 114 of the waist belt 111, which is disposed on the wearer's back.

Next, the flap separation type diaper 1-1 and the diaper base 121 pass through the wearer's part between the legs and move to the wearer's abdomen, and the fastening Velcro tape 123 not attached yet is attached to the diaper base fastening Velcro tape 114, so that the flap separation type diaper 1-1 can be worn through the waist belt 111 and the diaper base 121. In this case, the excreta inducing seat 25 and the feces accommodator 20 are located around the wearer's anus, and the urine accommodator 30 is located around the wearer's scrotum.

Now, the use state of the flap integration type diaper 1-2 of the diaper set 100-2 according to the present invention as shown in FIGS. 3 to 4b will be explained.

The flap integration type diaper 1-2 of the diaper set 100-2 according to the present invention includes the band flaps 6 and 7 formed integrally with left and right sides of the top sheet 2, and accordingly, the excreta inducing seat 25 is coupled to the seat accommodation bag 23 formed on the center portion 5 of the top sheet 2. In specific, the buttock rear surface stand 26 and the inclined surface 28 are insertedly coupled to the seat accommodation bag 23.

If the excreta inducing seat 25 is coupled to the seat accommodation bag 23, the release paper 41 attached to the inclined surface 28 of the excreta inducing seat 25 is removed, or in the case where the release paper (not shown) is attached to the adhesive layer applied to the undersides of the buttock rear surface stand 26 and the buttock side surface stands 27, the release paper is removed. In the state, the buttock rear surface stand 26 and the inclined surface 28 are insertedly coupled to the seat accommodation bag 23.

In the state where the excreta inducing seat 25 is coupled to the seat accommodation bag 23, the rear surface 5-2 passes through the wearer's buttocks and moves to the wearer's back, and the center portion 5 and the front surface 5-1 pass through the wearer's groin so that the front surface 5-1 moves to the lower abdomen of the wearer.

The adhesive members 11 of the band flaps 7 of the front surface 5-1 moving to the lower abdomen of the wearer are attached to the band flaps 6 of the rear surface 5-2 exposed to both sides of the wearer's buttocks, and in a state where both side band flaps 6 of the rear surface 5-2, to which the band flaps 7 of the front surface 5-1 are attached, move to cover the front surface 5-1 located on the abdomen of the wearer, the adhesive members 10 of the band flaps 6 are attached to the outer surface of the front surface 5-1, thereby finishing wearing the flap integration type diaper 1-2. In this case, the excreta inducing seat 25 and the feces accommodator 20 are located around the wearer's anus, and the urine accommodator 30 is located around the wearer's scrotum.

In the states where the flap separation type diaper 1-1 and the flap integration type diaper 1-2 of the diaper sets 100-1 and 100-2 according to the present invention are worn, if excreta or body discharge is expelled, it passes through the excreta inducing seat 25 and is accommodated in the feces accommodator 20 or introduced into the urine accommodator 30.

At the time when a waste material (excreta or body discharge) is discharged from the body of the wearer, the excreta inducing seat 25 prevents the waste material being discharged from coming into contact with the skin of the wearer and keeps the waste material permeating into the feces accommodator 20 and the urine accommodator 30 from coming into contact with the skin of the wearer, so that the skin of the wearer can be protected from the waste material, the wearer can be kept in a clean state, and the occurrence of skin troubles can be prevented.

In specific, even though not shown, the excreta inducing seat 25 having the adhesive layer 40 applied to the inclined surface 40 and the release paper 41 attached to the adhesive layer 40 or the excreta inducing seat (not shown) having the adhesive layer applied to the undersides of the buttock rear surface support 26 and the buttock side surface supports 27 and the release paper (not shown) attached to the adhesive layer may be attached directly to a diaper having no seat accommodation bag 23 or a typically used diaper.

That is, in the case where the excreta inducing seat 25 has the adhesive layer 40 applied to the inclined surface 40 and the release paper 41 attached to the adhesive layer 40, the release paper 41 is removed, and next, the excreta inducing seat 25 is attached to the typically used diaper.

Contrarily, in the case where the excreta inducing seat (not shown) has the release paper (not shown) attached to the adhesive layer applied to the undersides of the buttock rear surface support 26 and the buttock side surface supports 27, the release paper is removed, and next, the excreta inducing seat is attached to the typically used diaper.

If the excreta inducing seat 25 as shown in FIGS. 7a to 7c is provided for the diaper sets 100-1 and 100-2 according to the present invention, it turns over and is thus disposed in the seat accommodation bag 23 of the flap separation type diaper 1-1 or the flap integration type diaper 1-2.

Like this, if the excreta inducing seat 25 as shown in FIGS. 7a to 7c turns over and is thus disposed in the seat accommodation bag 23, the buttocks of the wearer are supported against the inclined surface 28 and the triangular buttock stand protrusion pieces 27-1, and accordingly, the wearer's anus is located on the open portion 29 to allow the wearer to easily expel feces, so that the feces is accommodated gently in the feces accommodator 20 through the open portion 29, and even though the wearer expels the feces, a clean and fresh state can be maintained in the diaper set. Further, as shown in FIG. 8, the detachable feces accommodator 35 is mounted directly on the open portion inner peripheral surface 30 of the excreta inducing seat 25 in the diaper sets 100-1 and 100-2 according to the present invention.

The excreta inducing seat 25 is configured to allow the underside of the open portion inner peripheral surface 30 to be connected to the vertically concave fastening surface 31 and the horizontally concave fastening surface 32, and in this case, the vertically concave fastening surface 31 has the concave fastening groove 31-1 formed thereon. The feces accommodator 35, which is coupled to the vertically concave fastening surface 31 on which the concave fastening groove 31-1 is formed and to the horizontally concave fastening surface 32, includes the cylindrical or square-shaped circular fastening protrusion rim 38 with the fastening protrusion piece 39 formed on the outer peripheral surface thereof, the flange 33 formed unitarily with the bottom end of the outer surface of the circular fastening protrusion rim 38, and the feces container 36 disposed unitarily with the underside of the flange 33 and having the absorbent member 36-1 filled therein.

If the detachable feces accommodator 35 is directly disposed in the open portion inner peripheral surface 30 of the excreta inducing seat 25, the excreta inducing seat 25 to which the feces container 36 is coupled may be installed on a typical diaper with no feces accommodator 20.

Like this, even though the excreta inducing seat 25 having the adhesive layer 40 applied to the inclined surface 40 or the excreta inducing seat having the adhesive layer applied to the undersides of the buttock rear surface support 26 and the buttock side surface supports 27 is attached to the typical diaper, the excreta inducing seat 25 prevents the waste material (excreta or body discharge) from coming into contact with the skin of the wearer, so that the skin of the wearer and the diaper set can be kept in a clean state and the occurrence of skin troubles can be prevented.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

The invention claimed is:

1. A diaper set comprising:
a diaper cover;
a flap separation type diaper disposed on top of the diaper cover and having a feces bag; and
a '⊏'-shaped excreta inducing seat disposed on the rear end of the feces bag of the flap separation type diaper,
wherein the diaper cover is separated into a waist belt part and a diaper base part, the flap separation type diaper comprises a seat accommodation bag disposed on the rear end of the feces bag, and the '⊏'-shaped excreta inducing seat has an inclined surface with a given angle ($\angle\theta$) slant upward and backward from the rear end of the underside thereof,
wherein the excreta inducing seat comprises: an adhesive layer applied to any one surface or two or more surfaces of the inclined surface, an underside of a buttock rear surface stand, and undersides of buttock side surface stands; and a release paper attached to the adhesive layer, and
wherein the excreta inducing seat comprises: triangular buttock stand protrusion pieces protruding from outer edges of the buttock side surface stands in parallel with each other in a same direction as the inclined surface thereof; and curvedly inclined surfaces formed on opposite surfaces of the buttock side surface stands to the triangular buttock stand protrusion pieces.

2. A diaper set comprising:
a flap integration type diaper having a feces bag; and
a '⊏'-shaped excreta inducing seat disposed on top of the feces bag of the flap integration type diaper,
wherein the flap integration type diaper comprises a seat accommodation bag disposed on the rear end of the feces bag, and the '⊏'-shaped excreta inducing seat has an inclined surface with a given angle ($\angle\theta$) slant upward and backward from the rear end of the underside thereof,
wherein the excreta inducing seat comprises: an adhesive layer applied to any one surface or two or more surfaces of the inclined surface, an underside of a buttock rear surface stand, and undersides of buttock side surface stands; and a release paper attached to the adhesive layer, and
wherein the excreta inducing seat comprises: triangular buttock stand protrusion pieces protruding from outer edges of the buttock side surface stands in parallel with each other in a same direction as the inclined surface thereof; and curvedly inclined surfaces formed on opposite surfaces of the buttock side surface stands to the triangular buttock stand protrusion pieces.

3. The diaper set according to claim 1, wherein the waist belt part of the diaper cover comprises: a waist belt of which width is relatively smaller than length; waist belt fastening tapes attached to both ends of the waist belt; and a pair of diaper base fastening tapes spaced apart from each other attached on one longitudinal end of the waist belt.

4. The diaper set according to claim 1, wherein the diaper base part of the diaper cover comprises: a diaper base with a relatively long length and a relatively shorter width than the length, the length and width of the diaper base being larger than the length and width of the flap separation type diaper; and fastening tapes attached to top and bottom ends thereof.

5. The diaper set according to claim 1, wherein the flap separation type diaper comprises a urine accommodator disposed on the front end of the feces bag.

6. The diaper set according to claim 1, wherein the given angle ($\angle\theta$) of the inclined surface of the excreta inducing seat is in the range between 1° and 45°.

7. The diaper set according to claim 1, wherein the excreta inducing seat comprises any one selected from a non-woven fabric, a fabric, and a paper sheet attached to any one surface or all surfaces among top of the buttock rear surface stand, tops of the buttock side surface stands, and the inclined surface.

8. The diaper set according to claim 1, wherein the excreta inducing seat has a curvedly concave groove formed on the top of the buttock rear surface stand.

9. A diaper set comprising:
a diaper cover;
a flap separation type diaper disposed on top of the diaper cover and having a feces bag; and
a '⊏'-shaped excreta inducing seat disposed on the rear end of the feces bag of the flap separation type diaper,
wherein the diaper cover is separated into a waist belt part and a diaper base part, the flap separation type diaper comprises a seat accommodation bag disposed on the rear end of the feces bag, and the '⊏'-shaped excreta inducing seat has an inclined surface with a given angle ($\angle\theta$) slant upward and backward from the rear end of the underside thereof and
wherein the excreta inducing seat comprises a feces accommodator detachably mounted on an open portion inner peripheral surface of the excreta inducing seat.

10. The diaper set according to claim 5, wherein the urine accommodator disposed on the front end of the feces bag comprises:
a urine bag attached to a top sheet of the flap separation type diaper;
an absorbent member filled in the urine bag; and
a urine accommodator cover sheet attached to top of the urine bag and having fine pores formed thereon.

11. The diaper set according to claim 1, wherein the triangular buttock stand protrusion pieces protruding from the outer edges of the buttock side surface stands each have a height (h2) between 5 and 30 mm.

12. The diaper set according to claim 9, wherein the feces accommodator detachably mounted on the open portion inner peripheral surface formed at the insides of the buttock side surface stands comprises:
a vertically concave fastening surface and a horizontally concave fastening surface connected to each other on the open portion inner peripheral surface and the underside of the excreta inducing seat, the vertically concave fastening surface having a concave fastening groove formed thereon;
a cylindrical or square-shaped circular fastening protrusion rim with a fastening protrusion piece formed on the outer peripheral surface thereof;
a flange formed unitarily with the bottom end of the outer surface of the circular fastening protrusion rim; and a feces container disposed unitarily with the underside of the flange and having an absorbent member filled therein.

13. The diaper set according to claim 2, wherein the flap integration type diaper comprises a urine accommodator disposed on the front end of the feces bag.

14. The diaper set according to claim 2, wherein the given angle ($\angle\theta$) of the inclined surface of the excreta inducing seat is in the range between 1° and 45°.

15. The diaper set according to claim 2, wherein the excreta inducing seat comprises any one selected from a non-woven fabric, a fabric, and a paper sheet attached to any one surface or all surfaces among top of the buttock rear surface stand, tops of the buttock side surface stands, and the inclined surface.

16. The diaper set according to claim 2, wherein the excreta inducing seat has a curvedly concave groove formed on the top of the buttock rear surface stand.

17. The diaper set according to claim 2, wherein the excreta inducing seat comprises a feces accommodator detachably mounted on an open portion inner peripheral surface of the excreta inducing seat.

* * * * *